US007740831B2

(12) United States Patent
Chiba et al.

(10) Patent No.: US 7,740,831 B2
(45) Date of Patent: Jun. 22, 2010

(54) COMPOSITIONS FOR POTENTIATING GLUTATHIONE

(75) Inventors: Tomohiro Chiba, Yokohama (JP); Takashi Naito, Yokohama (JP); Shioji Ishiwatari, Yokohama (JP)

(73) Assignee: Fancl Corporation, Kanagawa (JP)

( * ) Notice: Subject to any disclaimer, the term of this patent is extended or adjusted under 35 U.S.C. 154(b) by 1614 days.

(21) Appl. No.: 10/492,077

(22) PCT Filed: Sep. 11, 2002

(86) PCT No.: PCT/JP02/09247

§ 371 (c)(1),
(2), (4) Date: Oct. 18, 2004

(87) PCT Pub. No.: WO03/032966

PCT Pub. Date: Apr. 24, 2003

(65) Prior Publication Data

US 2006/0257351 A1    Nov. 16, 2006

(30) Foreign Application Priority Data

Oct. 9, 2001    (JP) ............................. 2001-311914

(51) Int. Cl.
*A61Q 5/08*   (2006.01)
*A61Q 9/00*   (2006.01)
*A01N 65/00*  (2009.01)
*A61K 36/68*  (2006.01)
*A61K 31/70*  (2006.01)
*A61K 31/05*  (2006.01)
*A61K 36/736* (2006.01)
*A61K 36/28*  (2006.01)

(52) U.S. Cl. .................... 424/62; 424/74; 424/725; 424/735; 424/737; 424/738

(58) Field of Classification Search .................. 424/62, 424/74, 725, 735, 737, 738; 514/25, 734
See application file for complete search history.

(56) References Cited

U.S. PATENT DOCUMENTS 4,990,330 A * 2/1991 Oyama ........................ 424/59

FOREIGN PATENT DOCUMENTS

| EP | 482766 | 4/1992 |
|---|---|---|
| EP | 1072265 | 1/2001 |
| JP | 60-27396 | 2/1985 |
| JP | 3-271226 | 12/1991 |
| JP | 03-271226 | 12/1991 |
| JP | 05-301811 | 11/1993 |
| JP | 7-215837 | 8/1995 |
| JP | 07-223940 | 8/1995 |
| JP | 7-223940 | 8/1995 |
| JP | 8-025883 | 1/1996 |
| JP | 08-119825 | 5/1996 |
| JP | 8-119825 | 5/1996 |
| JP | 2002-047178 | 2/2002 |
| JP | 2002-47178 | 2/2002 |
| KR | 2000011152 | 2/2000 |

OTHER PUBLICATIONS

Caterina De Ruvo et al.—Nutritional antioxidants as antidegenerative agents—International Journal of Developmental Neuroscience, 18(4-5), pp. 359-366 (2000).
Japanese Official Action—2003-535770.
De Ruvo, Caterina et al., "Nutritional antioxidants as anti-degenerative agents", International Journal of Developmental Neuroscience, 2000, vol. 18, Nos. 4 to 5 pp. 359 to 366.
Korean Patent Office issued a Korean notice of Allowance dated Dec. 23, 2009, Application No. 519952452229.

* cited by examiner

*Primary Examiner*—Humera N Sheikh
*Assistant Examiner*—Aradhana Sasan
(74) *Attorney, Agent, or Firm*—Young & Thompson

(57) ABSTRACT

A composition for potentiating glutathione, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof), and which further contains at least one member selected from among an S-containing compound that is a supply source of cysteine, a protein that contains cysteine and/or cystine, a yeast that contains cysteine and/or cystine, and a vitamin.

8 Claims, No Drawings

COMPOSITIONS FOR POTENTIATING GLUTATHIONE

TECHNICAL FIELD

The present invention relates to a composition containing a component that promotes the intracellular synthesis of glutathione. The present invention also relates to a composition for potentiating glutathione; a composition for promoting the production of a γ-glutamylcysteine synthetase, glutathione reductase, or cystine transporter; a composition for protection against ultraviolet radiation and/or for skin whitening; a composition for preventing cell damage or repairing cell damage caused by the promotion of intracellular synthesis of glutathione; a composition for improving or treating hepatic, renal, or pulmonary function; a composition for a disorder caused by the accumulation of lipid peroxides or the like; a composition for cataracts; or a composition for prevention and/or treatment of aging. Moreover, the present invention relates to a drug; an external agent for application to the skin; and a food such as a nutraceutical supplement, a functional food product, a health food, a specified health food, or a cosmeceutical product containing a component that promotes the intracellular synthesis of glutathione.

BACKGROUND ART

Glutathione is an antioxidant substance that is widely distributed in the living body, and is a tripeptide that consists of cysteine, glutamic acid, and glycine. As the main reducing agent in the living body, glutathione plays an important role in cell protection by various types of oxidation-reduction metabolism, as well as in xenobiotic metabolism, repair processes, and the like by means of the SH groups that are the active sites of glutathione. As the substrate of glutathione peroxidase, glutathione detoxifies peroxides such as hydrogen peroxide and lipid peroxides that are generated in the living body. Furthermore, by being oxidized itself, glutathione also acts to protect the living body from oxidative damages (e.g., by the above-mentioned peroxides, free radicals, and the like).

In cases where the equilibrium between oxidation promoting substances and the mechanism of the antioxidation ability is such that the former substances take precedence, oxidative stress occurs. Furthermore, if the living body is subjected to excessive oxidative stress, xenobiotic and the like, the glutathione in the living body is consumed to the point of exhaustion, so that normal cell function cannot be maintained. Pathological conditions that are caused by a decrease in the intracellular concentration of glutathione include cell damage, inflammation, darkening, production of spots or freckles caused by exposure to ultraviolet radiation, acute or chronic alcoholic liver damage, liver disease, chronic renal insufficiency, pulmonary disorders caused by tobacco smoking or the like, idiopathic pulmonary fibrosis, cataracts, ischemic heart disease, Parkinson's disease, Alzheimer's disease, gastric ulcers, adult respiratory organ impairment syndrome, immune deficiency, marrow formation insufficiency, acquired immune deficiency syndrome, latent viral infections, aging phenomena and cancerous changes accompanying physiological aging, and the like.

Glutathione formulations have been used to treat the above-mentioned pathological conditions caused by a decrease in the intracellular concentration of glutathione. However, depending on the organ, the oral administration of glutathione may not have the expected effect. Treatment by means of injection promises a greater effect than treatment by oral administration. However, such treatment involves a number of problems: namely, the administration involves pain, a visit to the hospital or clinic is required, and the like. Since the quantity of glutathione in cells depends on the quantity of cysteine that is present in the cells, S-containing compounds that are used to increase this quantity of cysteine in cells have been disclosed in recent years (JP 01-26516 A, JP 02-45420 A, JP 05-301811 A, and JP 08-319242 A).

For example, such compounds include N-acetylcysteine, L-2-oxothiazolidine-2-carboxylic acid, glutathione esters, and the like. However, depending on the organ, even such compounds have not been satisfactory in terms of the effect obtained.

The quantity of expression and the activity of enzymes that condense glutamic acid and cysteine and enzymes that synthesize γ-glutamylcysteine are known as another factor that determines the quantity of glutathione in cells. The activity and amount of expression of such enzymes are regulated by various factors such as thermal shock, tumor necrosis factor (TNF-α) cytokines such as interleukin 1, hormones such as insulin and glucocorticoid, heavy metals, factors relating to cell proliferation and cell cycle, and the like. Furthermore, antioxidant response elements are present in the 5' terminal regions of genes of these enzymes, so that the enzymes have a sequence that responds to antioxidant substances. The detailed mechanism is still not considered to be completely clear, but it has been reported that pulmonary edema induced by phosgene in mice can be prevented in advance by administering butylhydroxyanisole (which is used as an antioxidant in food products) and thus raising the glutathione concentration (Inhal. Toxical. 1999, 11 (9), pp. 855-871). However, it has not been reported that conventionally known antioxidants such as vitamin C, mannitol, amino acids (such as histidine) or antioxidants such as *Olea europaea* extracts (JP. 2000-128765 A, JP 2001-181632 A, and JP 2001-26518 A) and a hydrolysate of an *Olea europaea* extract (JP 09-78061 A) have a glutathione potentiating effect, and there is still no specific description of use in the prevention and treatment of the diseases cited above on the basis of such a mechanism of action.

DISCLOSURE OF THE INVENTION

In the conventional techniques of using S-containing compounds for supplying cysteine to cells in order to achieve a recovery from a decrease in the glutathione concentration, since such compounds are hardly incorporated into cells showing no decrease in the glutathione concentration, it has not been possible to significantly promote production of glutathione. Accordingly, it has likewise not been possible to obtain a sufficiently satisfactory effect in terms of the prevention of damage in the case where consumption of glutathione might be predicted, such as exposure to ultraviolet radiation, smoking, or ingestion of alcohols, or in the case of disease or the like that might conceivably be treated by increasing the glutathione concentration to level that is higher than an ordinary level.

It is an object of the present invention to provide an effective and highly safe composition for potentiating glutathione which increases the concentration of glutathione in the living body, and which is effective in the prevention and treatment of reduced function of each of various organs, as well as each of various damage and disorders, that are caused by a glutathione deficiency, and in the treatment of a disease or the like that might possible be treated by increasing the glutathione concentration to level that is higher than an ordinary level.

As a result of diligent research in order to achieve the above-mentioned object, the inventors of the present invention discovered that 2-(3,4-dihydroxyphenyl)ethanol (hereafter also referred to as "DPE") has an effect that promotes the intracellular synthesis of glutathione. The present invention was perfected on the basis of this finding.

That is, the present invention relates to the following compositions.

1. A composition for potentiating glutathione, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

2. A composition, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof), and which is used in at least one application selected from the group consisting of promotion of the production of γ-glutamylcysteine synthetase, promotion of the production of glutathione reductase, and promotion of the production of a cystine transporter.

3. A composition for protection against ultraviolet radiation and/or for skin whitening, which contains as a glutathione potentiating component at least one member selected, from the group consisting of 2-(3,4-dihydroxyphenyl)ethanol and a glycoside thereof.

4. A composition for protection against ultraviolet radiation and/or for skin whitening, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

5. A composition for prevention and/or for treatment of a disorder caused by a glutathione deficiency, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

6. A composition for prevention and/or for treatment of disorders caused by oxidative stress, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

7. A composition for prevention of cell damage and/or for repair of cell damage by promoting the intracellular synthesis of glutathione, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

8. A composition for improvement of liver function or for prevention and/or for treatment of a liver disorder, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

9. A composition for improvement of kidney function or for prevention and/or for treatment of a kidney disorder, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

10. A composition for prevention and/or for treatment of a disorder caused by a free radical or a peroxide such as a lipid peroxide, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

11. A composition for improvement of pulmonary function or for prevention and/or for treatment of pulmonary disorders, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

12. A composition for prevention and/or for treatment of cataracts, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

13. A composition for prevention and/or for treatment of aging, which contains at least one member selected from the group consisting of 2-(3,4-dihydroxyphenyl)ethanol or a glycoside thereof, a plant containing 2-(3,4-dihydroxyphenyl)ethanol or a glycoside thereof, an extract of said plant, a hydrolysate of said plant, and a hydrolysate of the extract of said plant (excluding *Olea europaea* and an extract thereof).

14. A composition according to any one of items 1, 2, and 4 to 13, wherein a plant containing 2-(3,4-dihydroxyphenyl)ethanol or a glycoside thereof is at least one member selected from the group consisting of *Olea europaea, Lamium album, Euphrasia officinalis, Prunus persica, Momordica grosvenorii, Rehmannia glutinosa, Plantago psyllium, Plantago asiatica, Echinacea angustifolia, Prunus* spp, *Plantago ovata, Prunus japonica* Thunb, *Conandron ramondioides* Siebold et Zucc, *Prunus mume, Prunus armeniaca, Osmanthus fragrans, Chlorella vulgaris, Celosia argentea* L., *Carpesium abrotanoides, Ballota nigra, Boschniakia rossica, Buddleja davidii, Castanopsis cuspidata* var. *sieboldii, Cistanche salsa, Conocephalum conicum, Digitails lanata, Digitalis lutea, Digitalis purpurea, Digitalis* sp, *Forsythia suspensa, Forsythia viridissima, Fraxinus japonica, Fraxinus ornus, Gleichenia glauca, Hemiphragma heterophyllum, Jasminum multiforum, Lantana camara, Leucosceptrum japonicum, Ligustrum japonicum, Ligustrum obtusifolium, Lysionotus pauciflorus, Magnolia obovata, Nyctanthes arbor-tristis, Osmanthus asiaticus, Penstemon procerus, Phtheirospermum japonicum, Plantago major, Prunus grayana, Quercus stenophylla, Ramonda myconi, Stachys sieboldii, Syringa reticulata, Syringa vulgaris, Jasminum sambac, Jasminum* offinale, *Ligustrum lucidum, Verbena officinalis* L., *Momordica charantia* L., and *Veronica persica*.

15. A composition according to any one of items 1 through 14, which further contains at least one member selected from among an S-containing compound that is a supply source of cysteine, a protein that contains cysteine and/or cystine, a yeast that contains cysteine and/or cystine, and a vitamin.

16. A composition according to any one of items 1 through 15, wherein the composition is for oral use or parenteral use.

17. A composition according to any of items 1 through 15, wherein the composition is for external use on the skin.

18. A composition according to any of items 1 through 17, wherein the composition is a drug.

19. A composition according to any one of items 1 through 15, wherein the composition is a food product.

20. A composition according to item 19, wherein the food product is a nutraceutical supplement, a functional food product, a health food, a specified health food, or a cosmeceutical product.

Hereinafter, the present invention will be described in detail.

The active ingredient discovered by the present invention, 2-(3,4-dihydroxyphenyl)ethanol, is represented by the following chemical formula (1).

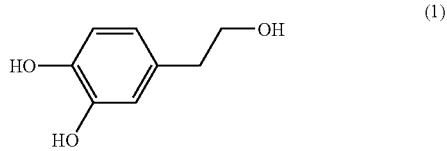

(1)

Examples of the glycoside include glycosides composed of monosaccharide, disaccharide, and trisaccharide. Examples of such saccharides include allose, galactose, and glucose.

Specific examples thereof includede 2-(3,4-dihydroxyphenyl)ethanol-1-O-β-D-allopyranoside, 2-(3,4-dihydroxyphenyl)ethanol-3'-O-β-D-galactopyranoside, 2-(3,4-dihydroxyphenyl)ethanol-1-O-β-D-glucopyranoside (see the following chemical formula (2)), 2-(3,4-dihydroxyphenyl)ethanol-3'-O-β-D-glucopyranoside (see the following chemical formula (3)) and 2-(3,4-dihydroxyphenyl)ethanol-4-O-β-D-glucopyranoside (see the following chemical formula (4)).

Examples of methods of obtaining 2-(3,4-dihydroxyphenyl)ethanol from natural materials include extraction from *Olea europaea*. Examples of plants containing DPE or a glycoside thereof include *Lamium album, Euphrasia officinalis, Prunus persica, Momordica grosvenorii, Rehmannia glutinosa, Plantago psyllium, Plantago asiatica, Echinacea angustifolia, Prunus* spp, *Plantago ovata, Prunus japonica* Thunb, *Conandron ramondioides* Siebold et Zucc, *Prunus mume, Prunus armeniaca, Osmanthus fragrans, Chlorella vulgaris, Celosia argentea* L., *Carpesium abrotanoides, Ballota nigra, Boschniakia rossica, Buddleja davidii, Castanopsis cuspidata* var. *sieboldii, Cistanche salsa, Conocephalum conicum, Digitails lanata, Digitalis lutea, Digitalis purpurea, Digitalis* sp, *Forsythia suspensa, Forsythia viridissima, Fraxinus japonica, Fraxinus ornus, Gleichenia glauca, Hemiphragma heterophyllum, Jasminum multiforum, Lantana camara, Leucosceptrum japonicum, Ligustrum japonicum, Ligustrum obtusifolium, Lysionotus pauciflorus, Magnolia obovata, Nyctanthes arbor-tristis, Osmanthus asiaticus, Penstemon procerus, Phtheirospermum japonicum, Plantago major, Prunus grayana, Quercus stenophylla, Ramonda myconi, Stachys sieboldii, Syringa reticulata, Syringa vulgaris, Jasminum sambac, Jasminum offinale, Ligustrum lucidum, Verbena officinalis* L., *Momordica charantia* L., and *Veronica persica*.

In addition, examples of plants containing DPE or a glycoside thereof include plants belonging to the following families.

*Calceolaria hypericina, Calceolaria* sp; *Cassinopsis sinensis, Cassinopsis madagascariensis, Cassinopsis* sp; *Cistanche salsa; Clerodendrum johnstonii, Clerodendrum myricoides; Digitalis ferruginea* ssp, *Digitalis grandiflora, Digitalis grandiflora* ssp. *ferruginea; Fraxinus angustifolia, Fraxinus insularis, Fraxinus oxycarba; Jasminum amplexicaule, Jasminum polyanthum; Lagotis stolonifera; Leonurus glaucens; Ligustrum pedunculare, Ligustrum purpurascens, Ligustrum* spp; *Lysionotus paucidlorus; Marrubium allysson; Momordica balsamina; Orobanche arenaria; Pedicularis plicata; Pedicularis semitorta, Pedicularis spicata, Pedicularis striata,* and *Pedicularis striata pall* ssp. *Arachnoidea*.

*Penstemon crandallii; Phlomis linearis; Plantago crassifolia, Plantago hostifolia, Plantago myosuros, Plantago* sp; *Premna corymbosa* var. *obtusifolia, Premna subscandens; Prostanthera melissifolia; Scrophularia nodosa, Scrophularia scopolii; Stachys lavandulifolia, Stachys officinalis; Syringa* sp; *Teucrium chamaedrys, Teucrium polium; Verbascum spinosum; Veronica bellidioides,* and *Veronica fuhsii*: and *Cistanche tubulosa; Markhamia lutea; Newbouldia laevis*; numerous plant spp.; *Orthocarpus densiflorus* (Orobanchaceae); *Retzia capensis; Salvadora calotropis; Sanango racemosum; Strobilanthus* sp; and *Trichomanes reniforme*.

In the above-mentioned plants, there can be utilized all parts that contain DPE or glycosides thereof. Examples of the parts include aerial parts such as leaves, stems, buds, flowers, woody parts, and bark parts (cortex); underground parts such as roots and tubers; seeds; and resins.

The above-mentioned plants can be used "as is", or as extracts, hydrolysate extracts, or hydrolyzed plants.

Examples of extraction method to obtain DPE used in the composition of the present invention from a natural substance include a method in which a dried product obtained by drying *Olea europaea* leaves, a homogenate thereof, a juice obtained by pressing *Olea europaea* leaves, or the like is subjected to extraction using an appropriate solvent, a hydrolysis treatment is performed (in some cases), the insoluble matter is removed by filtration or the like to remove the solvent from the solution, and the target substance is then obtained by an ordinary purification means such as column chromatography. In this case, it is desirable that the purification be performed by performing a bioassay in parallel, with the intracellular glutathione activity used as an indicator. Examples of solvents to be used in the extraction include: alcohols such as methanol, ethanol, propanol, and 1,3-butylene glycol; organic solvents such as ether, acetone, ethyl acetate, hexane, cyclohexane, dichloromethane, and chloroform; and water. Those solvents may be used singly, or may be used in mixtures containing two or more solvents. The extraction condition is not particularly limited, but the extraction can be performed at an ordinary temperature, for example, at a temperature of 5 to 95° C., preferably 15 to 85° C.

In regard to the pressure, the extraction may be performed at ordinary pressure, under pressure, or at a reduced pressure.

The extraction time varies according to the solvent selected. The extraction time may range from several minutes to several hours, and the extraction efficiency can be increased by performing a repeated extraction or a shaking extraction, by extending the extraction time, or the like.

Furthermore, the hydrolysis includes: decomposition by means of an enzyme such as esterase; decomposition by means of a microorganism such as lactic acid bacteria or yeast; decomposition by means of an acid such as hydrochloric acid, sulfuric acid, acetic acid, phosphoric acid, citric acid, lactic acid, tartaric acid, fumaric acid, or malic acid; and decomposition by means of an alkali such as sodium hydroxide or potassium hydroxide, and the like. The condition of hydrolysis is not particularly limited, but in the case where an enzyme or a microorganism is used, hydrolysis is ordinarily performed for approximately 5 to 24 hours at a temperature of 10 to 55° C. and a pH of 3 to 8, with the temperature and pH adjusted to values that are appropriate for the enzyme or microorganism used. In the case where hydrolysis is performed using an acid or an alkali, this hydrolysis is ordinarily performed for 0.5 to 24 hours at a concentration of 2 to 15 wt % and a temperature ranging from ordinary temperature to 60° C.

After the pH is adjusted if necessary, concentrated dried products can be obtained from such extracts or hydrolyzed extracts by known methods such as freeze-drying, distillation under reduced pressure, reduced-pressure or vacuum drying, and spray drying. The purification methods are not particularly limited, but for example, purification can be performed by normal-phase or reverse-phase chromatography, or purification can be performed by combining recrystallization, reprecipitation, decoloring treatments, deodorizing treatments, and the like.

The above-mentioned compound can also be obtained by a chemical synthesis method. For example, tetrahydrofuran (THF) and lithium aluminum hydride (LiAlH$_4$) are cooled to 0° C., 3,4-dihydroxyphenylacetic acid is added under agitation over a period of 20 to 30 minutes, and the temperature is gradually raised, followed by reflux for 6 hours. After the reaction solution is allowed to stand to cool, the reaction is stopped by adding purified water and 10% hydrochloric acid to the filtrate. Next, an extraction is performed using ethyl acetate, and the solvent is distilled off under reduced pressure, to thereby produce a dried product. The dried product is purified by silica gel column chromatography, to thereby produce DPE.

For example, DPE thus obtained is reacted with tetraacetyl-α-bromoglucose and the mixture is acidified by adding formic acid to produce a precipitate. Then, the precipitate is collected and concentrated by centrifugation, followed by drying in a vacuum desiccator using phosphorus (V) oxide as a dehydrating agent. The dried product is then dissolved in anhydrous methanol, and is deacetylated by adding a 28% solution of sodium methylate in methanol. Next, the solution is neutralized with 6N hydrochloric acid and the insoluble matter is filtered by means of a filter paper, followed by washing with methanol and water respectively. Then, the wash solution and the filtrate are combined, and the mixture is concentrated and evaporated, to thereby produce a crude DPE glucoside. Subsequently, the crude DPE glucoside is fractionated by ODS column chromatography and the resulting fractions are concentrated under reduced pressure. Then, the structures are determined by nuclear magnetic resonance (NMR), to thereby produce 2-(3,4-dihydroxyphenyl)ethanol-1-O-β-D -glucopyranocide (DPE-1-O-β-D-glucopyranocide) (CAS; 76873-99-9), 2-(3,4-dihydroxyphenyl)ethanol-3'-O-β-D-glucopyranocide (DPE-3'-O-β-D-glucopyranocide) (CAS; 142542-89-0), and 2-(3,4-dihydroxyphenyl)ethanol-4'-O-β-D-glucopyranocide (DPE-4'-O-β-D -glucopyranocide) (CAS; 54695-80-6).

DPE or a glycoside thereof that can be used in the present invention may be a compound in a plant, a compound in a plant extract, a compound in a hydrolysate obtained by hydrolyzing a plant or a plant extract, a compound obtained by purifying such a extract or a hydrolysate, or a chemically synthesized compound.

DPE or a glycoside thereof has a superior effect in promoting intracellular glutathione synthesis, and can be used as a glutathione potentiating agent. Furthermore, an even more superior effect can be obtained by using such a glutathione potentiating agent in combination with an S-containing compound that is a source of cysteine, a protein that contains cysteine and/or cystine, a yeast that contains cysteine and/or cystine, vitamins such as vitamin C and vitamin E, nicotinamide, calcium pantothenate, or the like.

Glutathione is a biological antioxidant substance that is present in plants, microorganisms, and various tissues of all mammals, and two types of glutathione, i.e., reduced glutathione and oxidized glutathione are known. The oxidized and reduced states of glutathione are regulated by a so-called redox cycle in glutathione peroxidase and glutathione reductase, so that the function of glutathione as an antioxidant substance is maintained. The site that is necessary in order to cause the operation of each function of glutathione is the SH group of the cysteine that is a constituent member of glutathione. Furthermore, generally known roles of glutathione include 1) the protection of SH groups in proteins, 2) scavenging of free radicals, 3) a role as a storage configuration of cysteine, and 4) regulation of basic cell processes such as DNA synthesis and immune function (Pharmacol. Ther. 1991. 52, pp. 287-305, Raven Press, New York, 1988. pp. 401-417; Proc. Natl. Acad. Sci. USA. 1990. 87, pp. 3343-3347; Exp. Cell. Res. 1997. 232, pp. 435-438).

Conceivable causes of the consumption and exhaustion or deficiency of glutathione include ordinarily occurring causes such as oxidative stress caused by active oxygen and the like, and causes such as radiation, ultraviolet light, alcohols, chemical substances, drugs, and heavy metals. Exposure to such risks on a daily basis results in a loss of the glutathione function described above, which may develop into disease. Furthermore, the production level of glutathione generally decreases with aging.

For example, in the case of acute respiratory distress syndrome, which is one of pulmonary disorders, the patients in most cases show decreases in glutathione levels, so that oxidative stress that causes oxidative damages in the lung cells is generated.

Examples of disorders that are associated with glutathione include: cell damage, skin roughening, inflammation, darkening, and production of spots and freckles caused by exposure to ultraviolet radiation; acute or chronic alcoholic liver damage caused by the excessive ingestion of alcohol; liver damage caused by xenobiotic or radiation; liver damage, hepatic insufficiency, or hepatitis caused by drugs, heavy metals, and chemical substances; a decrease in immune strength or autoimmune disorders caused by ultraviolet radiation; allergic disorders; immune disorders such as acquired immune deficiency syndrome; pulmonary disorders caused by tobacco smoking or the like; chronic renal insufficiency, cancerous changes and aging phenomena that accompany physiological aging; various types of arteriosclerotic disorders such as ischemic heart disorders, atherosclerosis, capillary impairment type hemolytic anemia, myocardial infarction, angina pectoris, cerebral infarction, cerebroateriosclerosis, and ischemia; cataracts; cerebral and neurological degenerative disorders (cerebral ischemia, amyotrophic lateral sclerosis, Alzheimer's disease, Parkinson's disease, Huntington's chorea); adult respiratory organ impairment syndrome; bone marrow formation insufficiency;

diabetes; nephrosis; hypertension; obesity; latent viral infections; gastric ulcers; and the like.

Intracellular glutathione levels in the cells of various organs such as the liver, lungs, kidneys, skin, and brain can be increased by promoting the synthesis of glutathione.

DPE or a glycoside thereof has an effect that promotes intracellular glutathione synthesis, and are useful in the prevention and treatment of a disorder caused by a decrease, deficiency, or exhaustion of glutathione.

A composition for potentiating glutathione is useful in prevention and treatment of a disorder caused by a deficiency or exhaustion of glutathione, a disorder caused by oxidative stress attributable to active oxygen or the like, a liver disorder such as acute or chronic alcoholic liver damage, hepatic insufficiency, or hepatitis, a kidney disorder, a disorder caused by a free radical or a peroxide such as a lipid peroxide, a pulmonary disorder caused by tobacco smoking or the like, cataracts, aging, and the like, and is also useful in improvement of the function of various organs such as improvement of liver function, or improvement of kidney function, improvement of lung function.

Examples of the "disorder caused by a deficiency or exhaustion of glutathione" include: acute or chronic alcoholic liver damage caused by the excessive ingestion of alcohol; liver damage caused by xenobiotic or radiation; liver damage, hepatic insufficiency; hepatitis caused by drugs, heavy metals, or chemical substances; lowering of immune strength or autoimmune disorders caused by ultraviolet radiation; allergic disorders; immune disorders such as acquired immune deficiency syndrome; ischemic heart disorders; cataracts; cerebral and neurological degenerative disorders (cerebral ischemia, amyotrophic lateral sclerosis, Alzheimer's disease, Parkinson's disease, Huntington's chorea); adult respiratory organ impairment syndrome; bone marrow formation insufficiency; diabetes; nephrosis; hypertension; obesity; atherosclerosis; latent viral infections; gastric ulcers; and the like.

Examples of the "disorder caused by oxidative stress" include: cell damage, inflammation, darkening, production of spots and freckles caused by exposure to ultraviolet radiation; pulmonary disorders caused by tobacco smoking and the like; chronic renal insufficiency; cataracts; ischemic heart disorders; gastric ulcers; cancerous changes and aging phenomena that accompany physiological aging and the like.

Examples of the "disorder caused by a free radical or a peroxide such as a lipid peroxide" include various types of arteriosclerotic disorders such as ischemic heart disorders, capillary impairment type hemolytic anemia, myocardial infarction, angina pectoris, cerebral infarction, cerebral arteriosclerosis, and cerebral ischemia, which are disorders of the so-called vascular system. Furthermore, roughening of the skin and the like are also included in this category.

The "S-containing compound that is a supply source of cysteine" is a compound that has an SH group in the molecule and includes substances that are non-cysteine substrates derived by a sulfur transfer reaction from methionine. Examples of compounds each having an SH group include but not limited to: glutathiones such as glutathione, acetylated glutathione, glutathione esters, glutathione hydrochlorides, glutathione phosphates, and glutathione sulfates or derivatives thereof; cysteines such as cysteine, N-acetylcysteine, cysteine hydrochloride, cysteine sulfate, and cysteine phosphate or derivatives thereof; mercaptoethanol; mercaptoacetic acid; mercaptopropionic acid; ammonium thiolactate; and monoethanolamine thiolactate. Examples of non-cysteine substrates include, but not limited to, L-2-oxothiazolidine-2-carboxylate and cystine.

Examples of the "protein and yeast containing cysteine and/or cystine" include whey, egg white, serum albumin, lactoalbumin, keratin, feather extracts, human hair extracts, and yeasts containing 1% or more glutathione (such as bread yeast and Tolar yeast). However, such a protein and yeast is not limited to these examples.

Examples of the "vitamins" include vitamin $B_1$ (thiamine) vitamin $B_2$ (riboflavin), vitamin $B_6$, vitamin $B_{12}$, vitamin A, vitamin. C (ascorbic acid), vitamin D, vitamin E, vitamin K, pantothenic acid, calcium pantothenate, biotin, folic acid, nicotinamide, and nicotinic acid. In addition, they include derivatives of those vitamins.

The "composition for protection against ultraviolet radiation and/or for skin whitening" refer to a composition that has a lightening effect on existing spots and freckles. Spots and freckles are caused by the excessive production of melanin and the deposition of this melanin. Accordingly, conventional techniques have aimed at the suppression of melanin production by seeking substances that inhibit tyrosinase, which is deeply involved in melanin production. However, the mechanism of action of the present invention differs from this, and is an action that depends on the promotion of intracellular synthesis of glutathione. Melanin includes two types, i.e., eumelanin which is black melanin, and pheomelanin which is light reddish-brown melanin. Intracellular glutathione acts on the pheomelanin production pathway in the process of melanin production. An effect has been experimentally reported in which the addition of glutathione to pigment producing cells causes an increase in the ratio of pheomelanin, so that the cells show a lightening in color (J. Invest. Dermatol. 1989. 93, pp. 100-107). Furthermore, it is known that glutathione promotes the effect of vitamin C in converting oxidized dark melanin into reduced light melanin. The improvement of pigment deposition in existing spots, freckles, and the like has been reported clinically (Japanese Journal of Clinical Dermatology, 1967. 21 (7), pp. 725-729). Pigment deposition in spots, freckles, and the like that have already been formed can be improved, and these spots or freckles can be lightened, by a glutathione potentiating effect.

Furthermore, something that should be especially noted here is that although DPE is already known as an antioxidant substance (Food Chem. Toxicol. 1994, 32 (1), pp. 31-36), DPE or a glycoside thereof in the "composition for preventing cell damage or repairing cell damage and/or repairing cell damage" of the present invention exerts an effect that indirectly alleviates or repairs damage in cellular membranes or the like that are attacked by active oxygen, a free radical, or the like that are generated from outside the cell due to an external cause such as ultraviolet radiation or carcinogenic substances, by promoting the intracellular synthesis of glutathione, and thus exerts an effect that differs from that of directly eliminating generated active oxygen as seen in a conventional antioxidant substance.

DPE or a glycoside thereof has an effect that promotes the production of γ-glutamylcysteine synthetase, glutathione reductase, or a cystine transporter, so that DPE or a glycoside thereof can be used as an active ingredient in compositions for promoting the production of γ-glutamylcysteine synthetase, glutathione reductase, or a cystine transporter. Furthermore, DPE or a glycoside thereof can further be used in combination with at least one member selected from the group consisting of proteins and yeasts that contain cysteine and/or cystine, and vitamins, to form a composition that is used for promoting the production of γ-glutamylcysteine synthetase, glutathione reductase, or a cystine transporter.

The γ-Glutamylcysteine synthetase, glutathione reductase, or a cystine transporter has a common consensus sequence in their respective coded genetic control regions. This is the sequence (RTGACnnnGC) which is called the antioxidant response element. Transcription factors such as Nrf2 and c-Jun control the expression of these genes in a cooperative manner via this sequence, and are thought to construct a system that protects the living body (Protein, Nucleic Acid, Enzyme, 1999, 44(15), pp. 2370-2376). In addition, examples of other enzymes that are controlled by the sequence include glutathione S-transferase, glucose 6-phosphoric acid dehydrogenase, ferritin, glutathione pump (GS-X pump), uridine diphosphoglucuronate transferase, and the like.

The γ-Glutamylcysteine synthetase is an enzyme that acts as a catalyst in the presence of magnesium when glutamic acid and cysteine (amino acids composing glutathione) are bonded. Since feedback inhibition of glutathione to this enzyme occurs, the activity of this enzyme is thought to be the rate-limiting step in glutathione synthesis.

The Glutathione reductase is an enzyme that irreversible reduces oxidized glutathione with the participation of NAD (P)H. This enzyme is thought to play an important role in the formation of an oxidation-reduction state in cells via glutathione.

The cystine transporter is a membrane protein that is present in a cell membrane, and has a high specificity for a basic amino acid, especially cystine (which is one of S-donors) and glutamic acid. The action of the carrier is as follows: namely, by undertaking the exchange transport of cystine and glutamic acid, the carrier ordinarily functions in a form that releases glutamic acid inside the cells and incorporates cystine outside the cells. The cystine that is transported into the cells participates in the production of glutathione via cysteine. In recent years, a 50-kilodalton cystine transporter (called xCT) has been cloned, and it has become clear that the carrier participates in the transport of cystine by forming a hetero-dimer with a 4F2 antigen heavy chain (4F2hc) which is known as an antigen activating a lymphocyte.

The composition for potentiating glutathione of the present invention may be used as a food product, an oral or parenteral drugs, or the like.

Examples of the above-mentioned food product include nutraceutical supplements, functional food products, health foods, specified health foods, cosmeceutical products, and the like.

Drug administration methods that can be used include both oral administration and parenteral administration. Examples of the parenteral administration include rectal administration, injection, and the like. The composition of the present invention can be administered in the form of customary drug formulation by mixing the composition with a solid or liquid non-toxic carrier for a drug that is suited to the method of administration. Examples of the form include: solid agents such as powders, spreading agents, granules, tablets, and capsules; liquid agents such as solution agents, suspending agents, and emulsions; freeze-dried formulations; or the like. Those formulations can be prepared by ordinary means. Examples of the non-toxic carrier for a drug that can be used include glucose, lactose, sucrose, starch, mannitol, dextrin, fatty acid glycerides, polyethylene glycol, hydroxyethylene starch, ethylene glycol, polyoxyethylene sorbitan fatty acid esters, amino acids, gelatin, albumin, water, physiological saline, and the like. If necessary, additives such as stabilizers, humectants, emulsifiers, binders, isotonic agents, and the like may be appropriately added. Furthermore, in regard to food products, the formulations may also be mixed with beverages such as juices.

The effective dosage of DPE or a glycoside thereof is appropriately selected and determined in accordance with the age, body weight, and symptoms of the subject, the administration route, administration schedule, formulation form and the like. For example, in the case of oral administration, an adult dosage is preferably 0.01 to 1,000 mg per day, particularly preferably 1 to 100 mg per day. Furthermore, in cases where the formulation contains an S-containing compound that is a supply source of cysteine, or a protein or yeast that contains cysteine and/or cystine, an adult dosage is preferably 5 to 5,000 mg per day, particularly preferably 50 to 500 mg per day. Vitamins may be appropriately mixed in accordance with the daily requirement amounts of these vitamins. For example, in the case of vitamin C, the adult dosage is 10 to 2,000 mg per day, particularly preferably 300 to 1,000 mg per day. The administration of such substances may also be divided into several administrations per day.

The effective dosage of a plant containing DPE or a glycoside thereof, an extract of said plant, or a hydrolysate of said plant or plant extract may be appropriately selected and determined according to the age, body weight, and symptoms of the subject, the administration route, administration schedule, formulation form, strength of the activity of the material, and the like. For example, in oral administration, the dosage of a hydrolysate of a plant extract (e.g., in the case of a hydrolyzed *Olea europaea* leaf extract) is preferably 0.01 to 5,000 mg per day, particularly preferably 1 to 300 mg per day. Furthermore, in the case where an S-containing compound that is a supply source of cysteine, or a protein or yeast that contains cysteine and/or cystine is mixed with the formulation, a dosage (in terms of the amount of cysteine) is preferably 5 to 5,000 mg per day, particularly preferably 50 to 500 mg per day. The administration of such a formulation may also be divided into several administrations per day. Vitamins may be appropriately mixed with such a formulation in accordance with the daily requirement amounts of these vitamins. For example, in the case of vitamin C, the adult dosage is 10 to 2,000 mg per day, particularly preferably 300 to 1,000 mg per day. In the case of nicotinamide, the adult dosage is 0.1 to 100 mg per day, particularly preferably 5 to 30 mg per day. The administration of such a formulation may also be divided into several administrations per day.

Furthermore, the composition for potentiating glutathione of the present invention may also be a product that is contained in a cosmetic, a medicated cosmetic, a drug, or the like (as referred to in the Pharmaceutical Affairs Law), in cases of external use on the skin. The composition may be used in a skin care product such as an emulsion, a cream, or a lotion, or in an ointment or the like. The dosage form thereof include a broad range of dosages such as aqueous solution systems, solubilized systems, emulsified systems, powder systems, oily liquid systems, gel systems, ointment systems, aerosol systems, water-oil two-layer systems, and water-oil-powder three-layer systems, but there is no particular limitation thereto.

The content of DPE or a glycoside thereof in a composition for external use on the skin is appropriately selected in accordance with differences in the symptoms involved. The content is about 0.001 to 20 wt %, preferably 0.01 to 5 wt % based on the total amount of the composition. Furthermore, in the case where such a composition contains an S-containing compound that is a supply source of cysteine, or a protein or yeast that contains cysteine and/or cystine, the content of such a substance (in terms of the amount of cysteine) is preferably 0.001 to 30 wt %, particularly preferably 0.1 to 10 wt %. Vitamins may be appropriately mixed with such a composition in accordance with the daily requirement amounts of these vitamins. For example, in the case of vitamin C, the content is preferably 0.001 to 40 wt %, particularly preferably 0.1 to 10 wt %. Of course, such a composition may be applied in 1 to 4 applications per day.

The content of a plant containing DPE or a glycoside thereof, an extract of said plant, or a hydrolysate of said plant or extract in a composition for external use on the skin is appropriately selected and determined in accordance with differences in the symptoms involved. In the case of *Syringa vulgaris* extract, the content is approximately 0.001 to 20 wt %, preferably 0.01 to 5 wt % based on the total amount of the composition. Furthermore, in the case where such a composition contains a compound that is a supply source of cysteine, or a protein or yeast that contains cysteine and/or cystine, the content (in terms of the amount of cysteine) is preferably 0.001 to 30 wt %, particularly preferably 0.1 to 10 wt %. Vitamins may be appropriately mixed with such a composition in accordance with the daily requirement amounts of these vitamins. For example, in the case of vitamin C, the content is preferably 0.001 to 40 wt %, particularly preferably 0.1 to 10 wt %. Of course, such a composition may be applied in 1 to 4 applications per day.

In the case where DPE or a glycoside thereof is used as a cosmetic material, the substance can be used as a cosmetic material by adding the substance to, for example, wheat germ oil or olive oil. For example, the content is 0.0001 to 20 wt %, preferably 0.01 to 5 wt % based on the mass of the wheat germ oil or *Olea europaea* oil.

In the case where a plant containing DPE or a glycoside thereof, an extract of said plant, or a hydrolysate of said plant or extract is used as a cosmetic material, the substance can be utilized as a cosmetic material by adding, for example, an extract or hydrolyzed extract of *Osmanthus fragrans* to wheat germ oil or *Olea europaea* oil. For example, the content of said plant extract or hydrolyzed plant extract is 0.1 to 60 wt %, preferably 0.5 to 50 wt % based on the weight of the wheat germ oil or *Olea europaea* oil.

DPE or a glycoside thereof has a low toxicity. Therefore, even in the case of long-term oral administration to rats for 100 days at a dosage of 1,000 mg/kg per day, there were no cases of mortality.

BEST MODE FOR CARRYING OUT THE INVENTION

EXAMPLES

Hereinafter, the present invention will be described specifically by way of examples, but the present invention is not limited thereto.

Example 1

Extraction from Plant and Hydrolysis of Plant

A 99.5% ethanol solution (3 L) was added to each of the following plants (500 g): an aerial part of Lamium album, an aerial part of *Euphrasia officinalis*, *Plantago psyllium* (whole plant body), a leaf of *Prunus persica*, a fruit of *Momordica grosvenorii*, *Plantago psyllium* seed (seed), *Rehmannia glutinosa* (root), a whole plant body of *Plantago asiatica*, a flower of *Echinacea angustifolia*, a leaf of *Prunus* spp, a seed of *Plantago ovata*, a seed of *Prunus japonica* Thunb, a whole plant body of *Conandron ramondioides* Siebold et Zucc, a fruit of *Prunus mume*, a seed of *Prunus armeniaca*, a flower of *Osmanthus fragrans*, a whole alga body of *Chlorella vulgaris*, a seed of *Celosia argentea* L., a culm of *Carpesium abrotanoides*, a fruit of *Ballota nigra*, a whole plant body of *Boschniakia rossica*, a leaf of *Buddleja davidii*, a leaf of *Castanopsis cuspidata* var. *sieboldii*, a whole plant body of *Cistanche salsa*, a whole alga body of *Conocephalum conicum*, a leaf of *Digitails lanata*, a leaf of *Digitalis lutea*, a leaf of *Digitalis purpurea*, a leaf of *Digitalis* sp, a leaf of *Olea europaea*, a fruit of *Forsythia suspensa*, a culm of *Forsythia viridissima*, a bark of *Fraxinus japonica*, a bark of *Fraxinus ornus*, an aerial part of *Gleichenia glauca*, a whole plant body of *Hemiphragma heterophyllum*, a whole plant body of *Jasminum multiforum*, a leaf of *Lantana camara*, a whole plant body of *Leucosceptrum japonicum*, a fruit of *Ligustrum japonicum*, a fruit of *Ligustrum obtusifolium*, a whole plant body of *Lysionotus pauciflorus*, a bark of *Magnolia obovata*, a whole plant body of *Nyctanthes arbor-tristis*, a flower of *Osmanthus asiaticus*, a leaf of *Penstemon procerus*, a culm of *Phtheirospermum japonicum*, a whole plant body of *Plantago major*, a whole plant body of *Prunus grayana*, a leaf of *Quercus stenophylla*, a leaf of *Ramonda myconi*, a tuber of *Stachys sieboldii*, a flower of *Syringa reticulata*, a leaf of *Syringa vulgaris*, a whole plant body of *Jasminum sambac, Jasminum offinale*, a seed of *Ligustrum lucidum*, a whole plant body of *Verbena officinalis* L., a fruit of *Momordica charantia* L., and a whole plant body of *Veronica persica*. Subsequently, extraction was performed by immersing the sample at room temperature overnight, and the extracted solution was concentrated under reduced pressure using an evaporator, to thereby remove an ethanol solvent.

The dry weights of respective extracts were 50.5, 10.4, 40.1, 20.3, 40.3, 68.8, 72.1, 52.6, 43.3, 46.1, 36.8, 29.7, 36.8, 34.6, 20.2, 25.4, 34.2, 78.7, 40.6, 26.8, 15.7, 39.3, 50.8, 60.9, 110.0, 40.7, 30.6, 30.4, 22.3, 77.8, 40.8, 80.7, 53.6, 44.6, 29.6, 44.7, 50.1, 72.3, 35.6, 43.6, 60.4, 25.6, 80.6, 59.4, 66.9, 37.5, 48.8, 60.1, 57.6, 10.2, 21.9, 19.6, 8.03, 45.6, 32.3, 36.9, 28.4, 37.0, and 43.4 g.

Next, in order to obtain a hydrolysate, a plant extract solution obtained by the same operation as the operation described above was adjusted to pH 2 with 1N sulfuric acid, and a hydrolysis treatment was performed by agitating the solution for 1 hour at 100° C. Subsequently, the solution was neutralized with sodium hydroxide and concentrated under reduced pressure by means of an evaporator. The residue was evaporated by freeze-drying, to thereby produce a hydrolysate.

The dry weights of respective hydrolysates were 55.5, 13.4, 46.1, 24.3, 47.3, 72.8, 90.1, 59.6, 48.3, 51.1, 45.8, 34.7, 42.1, 39.1, 25.9, 30.7, 39.1, 74.4, 47.3, 27.9, 23.4, 46.5, 48.8, 48.9, 72.0, 47.7, 37.4, 36.4, 27.3, 72.4, 44.8, 83.7, 57.6, 49.6, 35.6, 47.7, 53.1, 73.3, 36.6, 47.6, 58.4, 30.6, 78.6, 61.4, 64.9, 45.5, 46.8, 54.1, 56.6, 14.2, 22.3, 26.6, 12.03, 43.6, 53.3, 46.9, 35.4, 48.7, and 46.4 g. The resultant extracts and hydrolysates thereof were reprepared with an ethanol solvent so as to have a concentration of 10 mg/ml immediately prior to use, and the solutions were used in experiments.

Example 2

Extraction of 2-(3,4-dihydroxyphenyl)ethanol (DPE) from Plant 7.5 L of a 99.5% ethanol solution was added to 1,500 g each of leaves of *Olea europaea*, leaves of *Syringa vulgaris*, or leaves of *Osmanthus fragrans*, and an extraction was performed after immersing overnight at room temperature. Afterward, the extract solution was concentrated under reduced pressure by means of an evaporator to remove an ethanol solvent, to thereby produce respective extracts in amounts of 300, 285, and 264 g (dry weight). Next, fractionation was performed by LH-20 column chromatography using methanol, and the respective fractions were concentrated under reduced pressure by means of an evaporator to remove a methanol solvent, to thereby produce 25, 18, and 14 g (dry weight) of respective crude fractions. Next, fractionation was performed by silica gel column chromatography with a mixed solution of ethyl acetate:hexane (3:2), to thereby produce 6, 7, and 4 g (dry weight) of the respective crude fractions by a similar operation. Those fractions were dissolved in methanol again, and were further fractionated by ODS column chromatography with 13% methanol, and the resulting fractions were concentrated under reduced pressure, to thereby produce 0.4, 0.3, and 0.2 g of DPE respectively.

Example 3

Extraction of DPE from Plant Extract Hydrolysate 7.5 L of a 99.5% ethanol solution was added to 1,500 g each of leaves of *Olea europaea*, leaves of *Syringa vulgaris*, or leaves of *Osmanthus fragrans*, and an extraction was performed after immersing overnight at room temperature. Afterward, the extract solution was adjusted to pH 2 with 1N sulfuric acid, and a hydrolysis treatment was performed by agitating the solution for 1 hour at 100° C. Subsequently, the solution was neutralized with sodium hydroxide and concentrated under reduced pressure by means of an evaporator, followed by freeze-drying, to thereby produce hydrolysates of solvent extracts of *Olea europaea, Syringa vulgaris*, and *Osmanthus fragrans* leaves in amounts of 345, 384, and 322 g (dry weight), respectively. Next, those hydrolysates were dissolved in methanol, and the solution was fractionated by LH-20 column chromatography, followed by concentration under reduced pressure by means of an evaporator, to thereby produce 87, 71, and 55 g (dry weight) of respective crude fractions. Then, fractionation was performed by silica gel column chromatography with a mixed solution of ethyl acetate:hexane (3:2), to thereby produce 28, 21, and 15 g (dry weight) of respective crude fractions by a similar operation. Those fractions were further fractionated by ODS column chromatography with 13% methanol, and the resulting fractions were concentrated under reduced pressure, to thereby produce 2, 2, and 1 g of DPE, respectively.

Example 4

Chemical Synthesis of DPE

Tetrahydrofuran (THF, 200 ml) and lithium aluminum hydride $LiAlH_4$ (5.12 g:0.13 mol) were cooled to 0° C., and 3,4-dihydroxyphenylacetic acid (7.6 g:0.045 mol) was added thereto over a period of 20 to 30 minutes under agitation. Afterward, the temperature was gradually elevated, and reflux was performed for 6 hours. After the reaction solution was allowed to stand to cool, the reaction was stopped by adding ice water (100 ml) and 10% hydrochloric acid (100 ml). Next, an extraction operation was repeated 3 to 4 times with ethyl acetate (100 ml), and the ethyl acetate layer thus obtained was dried with anhydrous magnesium sulfate. Subsequently, the solvent was distilled off under reduced pressure, to thereby produce a dried product. The dried product was purified by silica gel column chromatography, to thereby produce DPE (4.5 g).

Example 5

Chemical Synthesis of DPE Glycoside 600 mg of DPE obtained in Example 4 and 4 g of tetraacetyl-α-bromoglucose were dissolved in 50 ml of dimethylformamide, and 2.7 g of potassium carbonate was added thereto, followed by reaction overnight at room temperature while agitating by means of a stirrer. The reaction solution was poured onto 300 g of ice, and was made acidic by adding formic acid to produce a precipitate. The precipitate was collected by centrifugation for 15 minutes at 1,000×g. The precipitate was washed once with distilled water, and was then dissolved in methanol, and the solution was evaporated by means of an evaporator, followed by drying in a vacuum desiccator using phosphorus (V) oxide as a dehydrating agent. The product was dissolved in 10 ml of anhydrous methanol and 1.6 ml of a 28% solution of sodium methylate in methanol was added thereto, followed by reaction for 20 minutes at room temperature, to thereby deacetylate the product. Next, the solution was neutralized with 6N hydrochloric acid, the insoluble matter was filtered using a filter paper, washing was respectively performed with methanol and water, and the wash solution and filtrate were combined. The mixture was concentrated and evaporated, to thereby produce 573 mg of a crude DPE glucoside. Then, the crude DPE glucoside was fractionated by ODS column chromatography, and the resulting fractions were concentrated under reduced pressure, to thereby produce 2-(3,4-dihydroxyphenyl)ethanol-1-O-β-D-glucopyranocide (DPE-1-O-β-D -glucopyranocide), 2-(3,4-dihydroxyphenyl)ethanol-3'-O-β-D -glucopyranocide (DPE-3'-O-β-D-glucopyranocide), and 2-(3,4-dihydroxyphenyl)ethanol-4'-O-β-D-glucopyranocide (DPE-4'-O-β-D -glucopyranocide) in amounts of 177, 214, and 166 mg, respectively.

Example 6

Measurement of Glutathione Activity

CCD 1059 normal human skin fibroblasts ($1.5 \times 10^5$ cells) (manufactured by Dainippon Pharmaceutical Co., Ltd.) were inoculated in a petri dish (manufactured by Nunc) with a diameter of 6 cm, and the cells were cultured in Dulbecco's modified Eagle's medium (DMEM) containing 10% deactivated fetal bovine serum (hereafter abbreviated to "FBS") for 3 days at 37° C. in the presence of 5% carbon dioxide gas. When the cells were 80% confluent, the medium was exchanged with DMEM containing 0.5% fetal bovine serum (hereafter abbreviated to "FBS" in some cases). After the cells were naturalized for 24 hours, the culture medium was removed by suction and exchanged with fresh DMEM containing 0.5% FBS and the test substances were dissolved in ethanol. Subsequently, the plant extracts and hydrolysates thereof obtained in Example 1 were added so as to have a final concentration of 100 µg/ml, DPE obtained in Examples 3 and 4 and the glycosides obtained in Example 5 were added so as to have final concentrations of 2.5, 5, 10, and 20 µg/ml, and the ethanol content in the culture medium was adjusted to 1% or less. The cells were then collected after being cultured for 24 hours. A group in which ethanol alone was added to the cells instead of the test substances so as to have a final concentration of 1% was used as a control, and the activities of the respective test substance groups were evaluated relative to the control with the activity of the control taken as 1. The collected cells were disrupted using sonication, and proteins were removed using metaphosphoric acid. Then, the solutions were again neutralized, to thereby produce samples used for glutathione measurement. The measurement of glutathione was performed using the method of Baker et al. (Anal. Biochem. 1990, 190, pp. 360-365). To describe the method briefly, reduced nicotinamide adenine dinucleotide phosphate (NADPH), glutathione reductase, and 5,5'-dithio-bis(2-nitrobenzoic acid) (DNTB) provided as a coloring agent were added to a 2-(N-morpholino)ethanesulfonate buffer (MES buffer), and the mixture was reacted with each measurement sample or a standard substance used to produce a calibration curve. Then, the absorbance at 405 nm was measured, and this was taken as the glutathione concentration. The results are shown in Tables 1 and 2. It is seen from Tables 1 and 2 that those plant extracts, plant extract hydrolysates, DPE, and DPE glycosides increase the intracellular concentration of glutathione compared to the control.

TABLE 1

Glutathione enhancing activity (plant extract and hydrolysate thereof)

| | Ratio to control | |
|---|---|---|
| Plant name | Plant extract | Hydrolysate of plant extract |
| Lamium album | 1.53 | 2.01 |
| Euphrasia officinalis | 1.66 | 1.75 |
| Plantago psyllium | 1.25 | 2.25 |
| Prunus persica | 1.54 | 2.11 |
| Momordica grosvenorii | 1.12 | 1.70 |
| Plantago psyllium seed | 1.45 | 2.36 |
| Rehmannia glutinosa | 1.19 | 1.88 |
| Plantago asiatica | 1.31 | 1.73 |
| Echinacea angustifolia | 1.36 | 1.56 |
| Prunus spp | 1.18 | 1.41 |
| Plantago ovata | 1.46 | 2.03 |
| Prunus japonica Thunb | 1.36 | 1.70 |
| Conandron ramondioides Siebold et Zucc | 1.27 | 1.96 |
| Prunus mume | 1.96 | 3.12 |
| Prunus armeniaca | 1.66 | 2.55 |
| Osmanthus fragrans | 178 | 2.74 |
| Chlorella vulgaris | 1.69 | 1.80 |
| Celosia argentea L. | 1.28 | 1.58 |
| Carpesium abrotanoides | 1.32 | 1.75 |
| Ballota nigra | 1.14 | 1.49 |
| Boschniakia rossica | 1.32 | 1.70 |
| Buddleja davidii | 1.30 | 1.66 |
| Castanopsis cuspidata var. sieboldii | 1.24 | 1.78 |
| Cistanche salsa | 1.22 | 1.98 |
| Conocephalum conicum | 1.22 | 1.65 |
| Digitails lanata | 1.16 | 1.44 |
| Digitalis lutea | 1.29 | 1.52 |
| Digitalis purpurea | 1.38 | 1.90 |
| Digitalis sp | 1.31 | 1.84 |
| Olea europaea | 1.78 | 3.22 |
| Forsythia suspensa | 1.58 | 2.40 |
| Forsythia viridissima | 1.08 | 1.41 |
| Fraxinus japonica | 1.35 | 1.90 |
| Fraxinus ornus | 1.56 | 2.63 |
| Gleichenia glauca | 1.36 | 1.79 |
| Hemiphragma heterophyllum | 1.10 | 1.18 |
| Jasminum multiforum | 1.06 | 1.57 |
| Lantana camara | 1.48 | 2.15 |
| Leucosceptrum japonicum | 1.19 | 1.42 |
| Ligustrum japonicum | 1.32 | 1.89 |
| Ligustrum obtusifolium | 1.23 | 1.76 |
| Lysionotus pauciflorus | 1.65 | 2.64 |
| Magnolia obovata | 1.22 | 1.51 |
| Nyctanthes arbortristis | 1.04 | 1.50 |
| Osmanthus asiaticus | 1.10 | 1.70 |
| Penstemon procerus | 1.06 | 1.35 |
| Phtheirospermum japonicum | 1.60 | 2.58 |

TABLE 1-continued

Glutathione enhancing activity (plant extract and hydrolysate thereof)

| | Ratio to control | |
|---|---|---|
| Plant name | Plant extract | Hydrolysate of plant extract |
| Plantago major | 1.40 | 2.20 |
| Prunus grayana | 1.39 | 1.70 |
| Quercus stenophylla | 1.07 | 1.47 |
| Ramonda myconi | 1.15 | 1.39 |
| Stachys sieboldii | 1.19 | 1.58 |
| Syringa reticulata | 1.33 | 2.06 |
| Syringa vulgaris | 1.31 | 2.11 |
| Jasminum sambac, Jasminum offinale | 1.43 | 2.69 |
| Ligustrum lucidum | 1.05 | 1.45 |
| Verbena officinalis L. | 134 | 1.99 |
| Momordica charantia L. | 1.20 | 1.58 |
| Veronica persica | 1.30 | 1.90 |

TABLE 2

Glutathione enhancing activity (compound)

| | Ratio to control | | | |
|---|---|---|---|---|
| Test substance | 2.5 µg/ml | 5 µg/ml | 10 µg/ml | 20 µg/ml |
| DPE | 1.36 | 1.85 | 2.33 | 2.74 |
| DPE-1-O-β-D-Glucopyranocide | 1.03 | 1.12 | 1.29 | 1.52 |
| DPE-3'-O-β-D-Glucopyranocide | 1.15 | 1.19 | 1.25 | 1.73 |
| DPE-4'-O-β-D-Glucopyranocide | 1.28 | 1.36 | 1.55 | 1.83 |

Example 7

Effect of Combined Use of S-Containing Compound (Cysteine)

Basically, an experiment was conducted in accordance with the method of Example 6. However, since it was desired to add an S-containing compound at an arbitrary concentration, the culture medium used in the case of this addition was DMEM that contains no S-containing compound (i.e., a medium that was free of methionine, cysteine, or cystine). The extracts of Olea europaea, Forsythia suspensa, Osmanthus fragrans, Osmanthus asiaticus, and Syringa vulgaris, and the hydrolysates thereof, that were obtained in Example 1 were respectively added to have a final concentration of 100 µg/ml, and DPE obtained in Examples 3 and 4 and DPE glycosides obtained in Example 5 were added to have a final concentration of 2.5 µg/ml. After 3 hours, cysteine whose pH was adjusted to the neutral region was added as an S-containing compound to have a final concentration of 200 or 400 µM. A comparison was made by calculation from the ratio relative to respective control groups in which only cysteine was added in the same amounts (groups in which only cysteine was added were taken as control groups in which the respective final concentrations of cysteine were 200 and 400 µM, and the activities of the respective test substance groups were evaluated as ratios relative to the control groups with the activities of the respective control groups taken as 1). The results are shown in Table 3. It is seen from Table 3 that the intracellular glutathione concentration was increased in a manner dependent on the cysteine concentration by adding cysteine (an S-containing compound) to the above-mentioned plant extracts, plant extract hydrolysates, DPE, and DPE glycosides. As a result, it is seen that those plants, hydrolysates thereof, DPE, and DPE glycosides participate in glutathione synthesis in cooperation with S-containing compounds.

TABLE 3

Combined effect with S-containing compound (cysteine)

| Test sample | Ratio to control | |
|---|---|---|
| | Cysteine 200 µM added group | Cysteine 400 µM added group |
| Olea europaea extract | 1.13 | 1.53 |
| Hydrolysate of Olea europaea extract | 1.73 | 2.65 |
| Forsythia suspensa extract | 1.08 | 1.45 |
| Hydrolysate of Forsythia suspensa extract | 1.68 | 2.35 |
| Osmanthus fragrans extract | 1.17 | 1.35 |
| Hydrolysate of Osmanthus fragrans extract | 1.62 | 1.96 |
| Osmanthus asiaticus extract | 1.36 | 1.66 |
| Hydrolysate of Osmanthus asiaticus extract | 1.85 | 2.78 |
| Syringa vulgaris extract | 1.28 | 1.69 |
| Hydrolysate of Syringa vulgaris extract | 1.52 | 2.91 |
| DPE | 1.25 | 1.89 |
| DPE-1-O-β-D-Glucopyranocide | 1.15 | 1.23 |
| DPE-3'-O-β-D-Glucopyranocide | 1.26 | 1.52 |
| DPE-4'-O-β-D-Glucopyranocide | 1.09 | 1.41 |

Example 8

Effect of Combined Use of S-Containing Compound (Cystine)

Basically, an experiment was conducted in accordance with the method of Example 6. However, since it was desired to add an S-containing compound at an arbitrary concentration, the culture medium used in the case of this addition was DMEM that contains no S-containing compound (i.e., a medium that was free of methionine, cysteine, and cystine). The extracts of Olea europaea, Forsythia suspensa, Osmanthus fragrans, Osmanthus asiaticus, and Syringa vulgaris, and the hydrolysates thereof, that were obtained in Example 1 were respectively added to have a final concentration of 100 µg/ml, and DPE obtained in Examples 3 and 4, and DPE glycosides obtained in Example 5 were added to have a final concentration of 10 µg/ml. At the same time, cystine was added as an S-containing compound to have a final concentration of 200 µM. A comparison was made by calculation from the ratio relative to respective control groups in which only cystine was added (groups in which only cystine was added were taken as control groups, and the activities of the respective test substance groups were evaluated as ratios relative to the control groups with the activities of the respective control groups taken as 1). The results are shown in Table 4. It is seen from Table 4 that the intracellular glutathione concentration was increased by adding cysteine (an S-containing compound) to the above-mentioned plant extracts, plant extract hydrolysates, DPE, and DPE glycosides. As a result, it is seen that the plants, hydrolysates thereof, DPE, and DPE glycosides participate in glutathione synthesis in cooperation with S-containing compounds.

TABLE 4

Combined effect with S-containing compound (cystine)

| Test sample | Ratio to control cystine 200 µM added group |
|---|---|
| Olea europaea extract | 1.64 |
| Hydrolysate of Olea europaea extract | 2.84 |
| Forsythia suspensa extract | 1.56 |
| Hydrolysate of Forsythia suspensa extract | 2.71 |
| Osmanthus fragrans extract | 1.61 |
| Hydrolysate of Osmanthus fragrans extract | 2.40 |
| Osmanthus asiaticus extract | 1.45 |
| Hydrolysate of Osmanthus asiaticus extract | 2.34 |
| Syringa vulgaris extract | 2.11 |
| Hydrolysate of Syringa vulgaris extract | 3.02 |
| DPE | 3.42 |
| DPE-1-O-β-D-Glucopyranocide | 1.42 |
| DPE-3'-O-β-D-Glucopyranocide | 1.56 |
| DPE-4'-O-β-D-Glucopyranocide | 1.68 |

Example 9

Effect on Liver Cell

Clone 9 human liver cells ($8 \times 10^6$ cells) (manufactured by Dainippon Pharmaceutical Co., Ltd.) were inoculated in a petri dish (manufactured by Nunc) with a diameter of 6 cm, and the cells were cultured in DMEM containing 10% deactivated FBS for 3 days at 37° C. in the presence of 5% carbon dioxide gas. When the cells were 80% confluent, the medium was exchanged with DMEM containing 0.5% FBS. After the cells were naturalized for 24 hours, the culture medium was removed by suction and exchanged with fresh DMEM containing 0.5% FBS, and the test substances were dissolved in ethanol. Subsequently, the extracts of Olea europaea, Forsythia suspensa, Osmanthus fragrans, Osmanthus asiaticus, and Syringa vulgaris, and the hydrolysates thereof, that were obtained in Example 1 were respectively added to have a final concentrations of 100 µg/ml, DPE obtained in Examples 3 and 4 and DPE glycosides obtained in Example 5 were added to have a final concentration of 10 µg/ml, and the ethanol content in the culture medium was adjusted to 1% or less. A group in which ethanol alone was added to the cells instead of the test substances so as to have a final concentration of 1% was used as a control, and the activities of the respective test substance groups were evaluated relative to the control with the activity of the control taken as 1. 24 hours after the addition, the cells were collected, and glutathione measurements were performed by the method described in Example 5. The results are shown in Table 5. It is seen from Table 5 that the intracellular glutathione concentration is also increased in liver cells compared to the control by adding the plant extracts, plant extract hydrolysates, DPE, and DPE glycosides discovered by the present invention.

TABLE 5

Effect on hepatocyte

| Test sample | Ratio to control |
|---|---|
| *Olea europaea* extract | 1.04 |
| Hydrolysate of *Olea europaea* extract | 1.12 |
| *Forsythia suspensa* extract | 1.06 |
| Hydrolysate of *Forsythia suspensa* extract | 1.21 |
| *Osmanthus fragrans* extract | 1.17 |
| Hydrolysate of *Osmanthus fragrans* extract | 1.34 |
| *Osmanthus asiaticus* extract | 1.13 |
| Hydrolysate of *Osmanthus asiaticus* extract | 1.19 |
| *Syringa vulgaris* extract | 1.04 |
| Hydrolysate of *Syringa vulgaris* extract | 1.22 |
| DPE | 1.16 |
| DPE-1-O-β-D-Glucopyranocide | 1.13 |
| DPE-3'-O-β-D-Glucopyranocide | 1.26 |
| DPE-4'-O-β-D-Glucopyranocide | 1.19 |

Example 10

Resistance to Active Oxygen Cell Damage Caused by Intracellular Glutathione Potentiation CCD 1059 normal human skin fibroblasts ($8 \times 10^4$ cells) (manufactured by Dainippon Pharmaceutical Co., Ltd.) were inoculated in a petri dish (manufactured by Nunc) with a diameter of 3.5 cm, and the cells were cultured in DMEM containing 10% deactivated fetal bovine serum (hereafter abbreviated to "FBS") for 1 day at 37° C. in the presence of 5% carbon dioxide gas. After the culture medium was exchanged with DMEM containing 0.5% FBS, the extracts of *Olea europaea, Forsythia suspensa, Osmanthus fragrans, Osmanthus asiaticus,* and *Syringa vulgaris*, and the hydrolysates thereof, that were obtained in Example 1 were respectively added to have a final concentration of 100 μg/ml, and DPE obtained in Examples 3 and 4 and DPE glycosides obtained in Example 5 were added to have a final concentration of 20 μg/ml. Then, preincubation was performed for 24 hours at 37° C., so that the intracellular glutathione concentration was increased. After 24 hours, the culture medium was removed by suction, and washing was performed twice with Hanks solution. The present test was performed in order to evaluate whether it was possible to alleviate the effects of the active oxygen that was generated by increasing the intracellular glutathione concentration, so that the plants, hydrolysates thereof, DPE, and DPE glycosides discovered by the present invention were completely removed after the preincubation.

After the cells were washed, rose bengal (which is a singlet oxygen generating agent) was dissolved in Hanks solution so as to have a final concentration of 50 μM, and was added to the cells. The cells were then irradiated for 10 minutes with visible light, so that the cells were exposed to singlet oxygen. The time for which the cells were immersed in Hanks solution and the time for which the cells were exposed to visible light were the same for all of the groups. After the exposure, the cells were again washed with Hanks solution, and the culture medium was exchanged with DMEM containing 10% FBS. After 3 days, the cells were counted by means of a Coulter counter, and the numbers of living cells were compared. In this comparison, an evaluation was performed with the number of cells in a non-exposed group that was not exposed to singlet oxygen taken as 100%. The results are shown in Table 6. It is seen from Table 6 that the survival rates of the respective groups exposed to singlet oxygen were improved (compared to a group that was not treated with any test substance (control)) by the addition of the above-mentioned plant extracts, hydrolysates thereof, DPE, and DPE glycosides. Since those plant extracts, hydrolysates thereof, DPE, and DPE glycosides were removed at the time of exposure, this indicated that it was possible to alleviate the effects of the active oxygen that was generated by increasing the intracellular glutathione concentration.

TABLE 6

Resistance against cell injury due to active oxygen caused by enhancing glutathione in cell

| Test sample | Survival rate (%: based on non-exposed group) |
|---|---|
| Test substance untreated group (control) | 28 |
| *Olea europaea* extract | 46 |
| Hydrolysate of *Olea europaea* extract | 58 |
| *Forsythia suspensa* extract | 38 |
| Hydrolysate of *Forsythia suspensa* extract | 47 |
| *Osmanthus fragrans* extract | 36 |
| Hydrolysate of *Osmanthus fragrans* extract | 62 |
| *Osmanthus asiaticus* extract | 34 |
| Hydrolysate of *Osmanthus asiaticus* extract | 51 |
| *Syringa vulgaris* extract | 45 |
| Hydrolysate of *Syringa vulgaris* extract | 55 |
| DPE | 61 |
| DPE-1-O-β-D-Glucopyranocide | 42 |
| DPE-3'-O-β-D-Glucopyranocide | 46 |
| DPE-4'-O-β-D-Glucopyranocide | 37 |

Example 11

Skin Whitening Test

Melanin suppressing activity was measured by the following test using the extracts of Lamium album, *Euphrasia officinalis, Plantago psyllium, Plantago psyllium* seeds, *Olea europaea, Forsythia suspensa, Conandron ramondioides* Siebold et Zucc, *Osmanthus fragrans, Osmanthus asiaticus, Syringa vulgaris, Verbena officinalis* L., and *Momordica charantia* L., and hydrolysates thereof obtained in Example 1, DPE obtained in Examples 3 and 4, and the DPE glycosides obtained in Example 5.

Cultured B16 melanoma cells derived from mouse provided as melanin producing cells were cultured in a minimum basic culture medium (MEM) to which FBS was added so as to have a final concentration of 10%. At a concentration of $3 \times 10^3$ cell/ml, those cells were inoculated in a 6-well plate (6 ml in each well), and were cultured in a $CO_2$ incubator for 5 days, after which the culture medium was exchanged. The plant extracts and hydrolysates thereof obtained in Example 1 were added at respective concentrations of 100 μg/ml, and DPE obtained in Examples 3 and 4 and DPE glycosides obtained in Example 5 were added at respective concentrations of 20 μg/ml. Then, after further culturing for 3 days under the same conditions, the cells were washed and stripped by a scraper treatment. The cells were then solubilized with sodium dodecylsulfate (SDS), and the absorbance values at 475 nm and 260 nm were measured (these values were taken as $S_{475}$ and $S_{260}$). The melanin suppression rate was calculated using the following Equation 1, with the absorbance values at 475 nm and 260 nm obtained for cells cultured in a culture medium to which no test substances were added taken as $C_{475}$ and $C_{260}$, respectively. 3 mM vitamin C and 3 mM kojic acid were used as positive controls. The results are shown in Tables 7 and 8. As is shown in Tables 7 and 8, the production of melanin is suppressed by the addition of the test substances, so that the test substances show a skin whitening effect.

Expression 1

Melanin suppression rate (%)=1−[($S_{475}$/$S_{260}$)/($C_{475}$/$C_{260}$)]×100

TABLE 7

Skin whitening Test

| Test substance | Melanin suppression rate | |
|---|---|---|
| | Plant extract | Hydrolysate of plant extract |
| Vitamin C 3 mM | 23.0% | 23.0% |
| Kojic acid 3 mM | 39.9% | 39.9% |
| *Lamium album* | 59.6% | 64.6% |
| *Euphrasia officinalis* | 27.9% | 45.1% |
| *Plantago psyllium* | 25.7% | 32.6% |
| *Plantago psyllium* seed | 40.8% | 51.9% |
| *Olea europaea* | 32.1% | 49.3% |
| *Forsythia suspensa* | 20.6% | 28.3% |
| *Conandron ramondioides* Siebold et Zucc | 56.4% | 71.4% |
| *Osmanthus fragrans* | 28.8% | 36.6% |
| *Osmanthus asiaticus* | 25.4% | 33.9% |
| *Syringa vulgaris* | 54.3% | 69.3% |
| *Verbena officinalis* L. | 33.6% | 48.5% |
| *Momordica charantia* L. | 39.6% | 55.6% |

TABLE 8

Skin whitening test (compound)

| Test substance | Melanin suppression rate |
|---|---|
| Vitamin C 3 mM | 23.0% |
| Kojic acid 3 mM | 39.9% |
| DPE | 52.3% |
| DPE-1-O-β-D-Glucopyranocide | 24.6% |
| DPE-3'-O-β-D-Glucopyranocide | 32.3% |
| DPE-4'-O-β-D-Glucopyranocide | 35.4% |

Example 12

Measurement of Cystine Transporter (xCT) Production Ability by Western Blotting

CCD 1059 normal human skin fibroblasts (1.5×10⁵ cells) (manufactured by Dainippon Pharmaceutical Co., Ltd.) were inoculated in a petri dish (manufactured by Nunc) with a diameter of 6 cm, and the cells were cultured in DMEM containing 10% deactivated FBS for 3 days at 37° C. in the presence of 5% carbon dioxide gas. When the cells were 80% confluent, the medium was exchanged with DMEM containing 0.5% FBS. After the cells were naturalized for 24 hours, the culture medium was removed by suction, and the culture medium was exchanged with fresh DMEM containing 0.5% FBS. Then, the extracts of *Olea europaea, Forsythia suspensa, Osmanthus fragrans, Osmanthus asiaticus,* and *Syringa vulgaris,* and the hydrolysates thereof that were obtained in Example 1 were added so as to have a final concentration of 100 μg/ml, DPE obtained in Examples 3 and 4 and the DPE glycosides obtained in Example 5 were added so as to have a final concentration was 20 μg/ml, and the ethanol content in the culture medium was adjusted to 1% or less. After a further 24 hours, the cells were collected. Using a group in which ethanol only was added to the cells instead of the test substances so as to have a final concentration of 1% as a control, the activities of the respective test substance groups were evaluated relative to the control with the activity of the control taken as 1. The collection of the cells was accomplished as follows: a solubilizing agent (0.5% NP-40, 50 mM Tris-HCl (pH 7.5), 120 mM NaCl, 1 mM $Na_3VO_4$) was added, the mixture was shaken for 30 minutes at 4° C., the solubilizing agent was collected, and the cell fragments were removed by centrifugation for 30 minutes at 15,000 rpm. The supernatant was dialyzed with distilled water, and then evaporated by freeze-drying.

Next, this product was dissolved in 400 μl of distilled water, and a protein determination was performed by the Lowry method. Afterward, a correction of the protein amount between samples was performed. An arbitrary amount of sample buffer was added to the resulting product, and this was used as a sample in Western blotting. After the protein in the sample was separated by SDS-PAGE, transferring to a nitrocellulose film was performed. The transferred nitrocellulose film was immersed in a blocking solution (PBS containing 5% skim milk), and blocking was performed for 1 hour at room temperature. After washing with a wash solution (PBS containing 0.1% bovine serum albumin and 0.05% polyoxyethylene (20) sorbitan monolaurate), the film was immersed in a primary antibody (polyclonal antibody for xCT adjusted to 1 mg/ml with the wash solution), and a reaction was performed overnight at room temperature. After washing, the film was immersed in a secondary antibody (biotinylated anti-rabbit immunoglobulin G adjusted to 1 mg/ml with the wash solution), and a reaction was performed for 1 hour at room temperature. After washing, the film was immersed in an enzyme solution (alkaline phosphatase avidin D adjusted to 1 mg/ml with the wash solution), and a reaction was performed for 1 hour at room temperature. After washing, the film was immersed in a substrate solution (BCIP/NBT substrate kit (manufactured by Vector Laboratories, Inc.), and a reaction was performed for 15 minutes at room temperature. After the completion of the reaction, the coloring intensity was measured using image analysis software (ImageMaster 1D, manufactured by Amersham Pharmacia Biotech Co.).

The measurement results obtained for the xCT production ability of the cell extracts by Western blotting are shown in Table 9. It is seen from Table 9 that the above-mentioned plant extracts, hydrolysates thereof, DPE, and DPE glycosides promoted the expression of xCT compared to the control.

TABLE 9

Measurement of cystine transporter (xCT) production ability by Western blotting

| Test Sample | Amount of xCT expression (Relative to control) |
|---|---|
| *Olea europaea* extract | 2.1 |
| Hydrolysate of *Olea europaea* extract | 4.2 |

TABLE 9-continued

Measurement of cystine transporter (xCT) production ability by Western blotting

| Test Sample | Amount of xCT expression (Relative to control) |
|---|---|
| Forsythia suspensa extract | 1.9 |
| Hydrolysate of Forsythia suspensa extract | 2.8 |
| Osmanthus fragrans extract | 2.4 |
| Hydrolysate of Osmanthus fragrans extract | 3.9 |
| Osmanthus asiaticus extract | 1.7 |
| Hydrolysate of Osmanthus asiaticus extract | 2.4 |
| Syringa vulgaris extract | 2.0 |
| Hydrolysate of Syringa vulgaris extract | 4.3 |
| DPE | 4.8 |
| DPE-1-O-β-D-Glucopyranocide | 1.7 |
| DPE-3'-O-β-D-Glucopyranocide | 1.3 |
| DPE-4'-O-β-D-Glucopyranocide | 1.5 |

Example 13

Measurement of Promoting Activity of γ-glutamylcysteine Synthetase Production by RT-PCT (Reverse transcriptase-polymerase Chain Reaction)

CCD 1059 normal human skin fibroblasts ($1.5 \times 10^5$ cells) (manufactured by Dainippon Pharmaceutical Co., Ltd.) were inoculated in a petri dish (manufactured by Nunc) with a diameter of 6 cm, and the cells were cultured in DMEM containing 10% deactivated FBS for 3 days at 37° C. in the presence of 5% carbon dioxide gas. When the cells were 80% confluent, the medium was exchanged with DMEM containing 0.5% FBS. After the cells were naturalized for 24 hours, the culture medium was removed by suction, and the culture medium was exchanged with fresh DMEM containing 0.5% FBS. Then, the extracts of Olea europaea, Forsythia suspensa, Osmanthus fragrans, Osmanthus asiaticus, and Syringa vulgaris, and the hydrolysates thereof that were obtained in Example 1 were added so as to have a final concentration of 100 µg/ml, DPE obtained in Examples 3 and 4 and the DPE glycosides obtained in Example 5 were added so as to have a final concentration of 20 µg/ml, and the ethanol content in the culture medium was adjusted to 1% or less. After 8 hours, total RNA was collected by using TRIZOL reagent (Life Technologies Oriental, Inc.) following a protocol.

Gamma-glutamyl cysteine synthetase mRNA and G3PDH mRNA expression promoting activities were measured with RT-PCR high (Toyobo Co., Ltd.) using the collected total RNA. The G3PDH gene is known as a housekeeping gene and expresses in all cells constantly, so that the gene is widely used as a control gene. The following primers were used for PCR: 5'-TGA AAC TCT GCA AGA GAA GOG G-3' (SEQ ID NO: 1) and 5'-GCT TCA TCT GGA AAG AGO AGG G -3' (SEQ ID NO: 2) (gamma-glutamyl cysteine synthetase); and 5'-ACC ACA GTC CAT GCC ATC AC-3' (SEQ ID NO: 3) and 5'-TCC ACC ACC CTG TTG CTG TA-3' (SEQ ID NO: 4) (G3PDH). The conditions of the PCR reaction were as follows: specifically, γ-glutamylcysteine synthetase was treated for 7 minutes at 94° C., then, a treatment for 1 minute at 94° C., 1 minute at 56° C., and 1 minute at 74° C. was repeated 35 times. Subsequently, a treatment was performed for 10 minutes at 74° C., and the product was stored at 4° C. In the case of G3PDH, meanwhile, a treatment was performed for 7 minutes at 94° C., then, a treatment for 1 minute at 94° C., 1 minutes at 58° C., and 1 minute at 74° C. was repeated 20 times. Subsequently, a treatment was performed for 10 minutes at 74° C., and the product was stored at 4° C. The RT-PCR products were subjected to electrophoresis stained with ethidium bromide, and photographed with a digital camera. Then, the intensity of staining was measured using image analysis software ImageMaster 1D (manufactured by Amersham Pharmacia Biotech Co.). The group in which no test substances were added (1% ethanol) was taken as a control, and the amount of expression was evaluated by a comparison of the amounts of expression in cases where test substances were added (with a value obtained by dividing the staining intensity of the γ-glutamylcysteine synthetase mRNA by the staining intensity of G3PDH taken as 1). It is seen from Table 10 that these plant extracts, hydrolysates thereof, DPE, and DPE glycosides promote the expression of γ-glutamylcysteine synthetase compared to the control.

TABLE 10

Measurement of gamma-glutamyl cysteine synthetase production promoting activity by RT-PCR (Reverse transcriptase-polymerase chain reaction)

| Test Sample | Gamma-glutamyl cysteine synthetase/G3PDH (Relative to control) |
|---|---|
| Olea europaea extract | 4.2 |
| Hydrolysate of Olea europaea extract | 7.5 |
| Forsythia suspensa extract | 3.6 |
| Hydrolysate of Forsythia suspensa extract | 8.5 |
| Osmanthus fragrans extract | 3.7 |
| Hydrolysate of Osmanthus fragrans extract | 7.4 |
| Osmanthus asiaticus extract | 3.4 |
| Hydrolysate of Osmanthus asiaticus extract | 6.2 |
| Syringa vulgaris extract | 5.3 |
| Hydrolysate of Syringa vulgaris extract | 6.8 |
| DPE | 8.2 |
| DPE-1-O-β-D-Glucopyranocide | 3.1 |
| DPE-3'-O-β-D-Glucopyranocide | 3.8 |
| DPE-4'-O-β-D-Glucopyranocide | 4.5 |

Examples of formulation are shown below.

[Tablet Production]

Tablets with the following composition were produced by an ordinary method using cystine and the Olea europaea hydrolysate obtained in Example 1.

| (Component) | (Composition; wt %) |
|---|---|
| Olea europaea hydrolysate (dry weight) | 16 |
| Cystine | 16 |
| Vitamin C | 20 |
| Nicotinamide | 1 |
| Cellulose | 20 |
| Indigestible dextrin | 24 |
| Sucrose fatty acid ester | 3 |

[Tablet production]

Tablets with the following composition were produced by an ordinary method using 2-(3,4-dihydroxyphenyl)ethanol and glutathione-containing yeast obtained in Examples 3 and 4.

| (Component) | (Composition; wt %) |
| --- | --- |
| 2-(3,4-Dihydroxyphenyl)ethanol | 10 |
| Lactose | 62 |
| Cornstarch | 17 |
| Guar gum | 1 |
| Glutathione-containing yeast | 10 |

[Juice production]

Juice with the following composition was produced by an ordinary method.

| (Component) | (Composition; wt %) |
| --- | --- |
| Fructose glucose liquid sugar | 5.00 |
| Citric acid | 10.4 |
| Vitamin C | 0.50 |
| Perfume | 0.02 |
| Coloring agent | 0.10 |
| *Syringa vulgaris* extract (dry weight) | 10.0 |
| Purified water | 73.98 |

[Skin care product (hand cream) production]

A hand cream with the following composition was produced by an ordinary method.

| (Component) | (Composition; wt %) |
| --- | --- |
| Isopropyl isostearate | 8.0 |
| *Jojoba* oil | 6.0 |
| Cetanol | 8.0 |
| Alcohol stearate | 2.0 |

| (Component) | (Composition; wt %) |
| --- | --- |
| Polyoxyethylene laurylether | 1.5 |
| Propylene glycol | 6.0 |
| Sorbitol | 1.0 |
| Paraven | 0.4 |
| 2-(3,4-Dihydroxyphenyl)ethanol | 0.8 |
| Vitamin E | 0.5 |
| Vitamin C | 1.0 |
| Perfume | 0.1 |
| Purified water | 64.7 |

INDUSTRIAL APPLICABILITY

As is clear from the above description, the composition of the present invention has a glutathione potentiating activity, so that the composition can increase the amount of glutathione that is supplied in the living body. Accordingly, the composition is useful in the prevention and treatment of a disorder that is caused by a glutathione deficiency, and is especially useful in the treatment of a liver disorder such as acute or chronic alcoholic liver damage, hepatic insufficiency, or hepatitis, and in the improvement of liver function. Furthermore, the composition of the present invention can also be used in the prevention or treatment of a disorder caused by oxidative stress attributable to active oxygen or the like, especially cell damage, inflammation, darkening, spots, and freckles caused by exposure to ultraviolet radiation, a pulmonary disorder caused by tobacco smoking or the like, improvement of pulmonary function, cataracts, and aging changes that accompany physiological aging. Furthermore, the glutathione potentiating activity of the compositions of the present invention is greatly increased by combined use with an S-containing compound that is a supply source of cysteine, or a protein or yeast that contains cysteine and/or cystine. Accordingly, the composition of the present invention is useful as a composition that has an even more superior effect in the prevention or treatment of each of the above-mentioned disorders.

The invention claimed is:

1. A method of skin whitening, said method comprising administering, to a subject in need thereof, a composition comprising:

2-(3,4-dihydroxyphenyl)ethanol or a glycoside thereof; and

200 μM-400 μM cysteine or cystine.

2. The method of claim 1, wherein said composition is administered externally to the skin.

3. The method of claim 1, wherein said composition is a food product.

4. The method of claim 1, wherein said composition is in the form of a tablet.

5. A method of skin whitening, said method comprising administering, to a subject in need thereof, a composition comprising:

an extract of a plant selected from *Lamium album, Euphrasia officinalis, Plantago psyllium, Olea europaea, Forsythis suspense, Conandron ramondioides Siebold et Zucc, Osmanthus fragrans, Osmanthus asiaticus, Syringa vulgaris, Verbena officinalis* L., and *Momordica charantia* L., or a glycoside thereof; and 200 μM-400 μM cysteine or cystine.

6. The method of claim 5, wherein said composition is administered externally to the skin.

7. The method of claim 5, wherein said composition is a food product.

8. The method of claim 5, wherein said composition is in the form of a tablet.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 1
tgaaactctg caagagaagg gg                                            22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 2
gcttcatctg gaaagaggag gg                                            22
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 3
accacagtcc atgccatcac                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 4
tccaccaccc tgttgctgta                                               20
```